United States Patent [19]

Schaldach

[11] Patent Number: 5,186,169

[45] Date of Patent: Feb. 16, 1993

[54] COMMON SIGNAL TRANSMISSION PATH CARDIAC PACEMAKER WITH SWITCHABLE CAPACITORS

[75] Inventor: Max Schaldach, Erlangen, Fed. Rep. of Germany

[73] Assignee: Biotronik Mess- und Therapiegeräte GmbH & Co., Berlin, Fed. Rep. of Germany

[21] Appl. No.: 543,817

[22] PCT Filed: Nov. 14, 1988

[86] PCT No.: PCT/DE88/00723

§ 371 Date: Jul. 12, 1990

§ 102(e) Date: Jul. 12, 1990

[87] PCT Pub. No.: WO89/04192

PCT Pub. Date: May 18, 1989

[30] Foreign Application Priority Data

Nov. 13, 1987 [DE] Fed. Rep. of Germany ....... 3739091

[51] Int. Cl.⁵ .............................................. A61N 1/362
[52] U.S. Cl. ................................................ 128/419 PG
[58] Field of Search .................... 128/419 PG, 419 PT

[56] References Cited

U.S. PATENT DOCUMENTS

| | | | |
|---|---|---|---|
| 4,399,820 | 8/1983 | Wirtzfeld et al. | 128/419 PG |
| 4,543,955 | 10/1985 | Schroeppel | 128/419 PG |
| 4,549,548 | 10/1985 | Wittkampf et al. | 128/419 PG |
| 4,628,934 | 12/1986 | Pohndorf et al. | 128/419 PG |
| 4,681,111 | 7/1987 | Silvian | 128/419 PT |
| 4,726,379 | 2/1988 | Altman et al. | 128/419 PG |
| 4,877,032 | 10/1989 | Heinze et al. | 128/419 PG |

Primary Examiner—Kyle L. Howell
Assistant Examiner—Kennedy J. Schaetzle
Attorney, Agent, or Firm—Spencer, Frank & Schneider

[57] ABSTRACT

Implantable cardiac pacemaker with a plurality of inputs for signal reception and switchable capacitors connected to these inputs, whereby analog signals obtained through signal receivers from external and/or internal sources are consecutively transmitted on a common signal transmission path inside and/or outside the cardiac pacemaker housing.

21 Claims, 8 Drawing Sheets

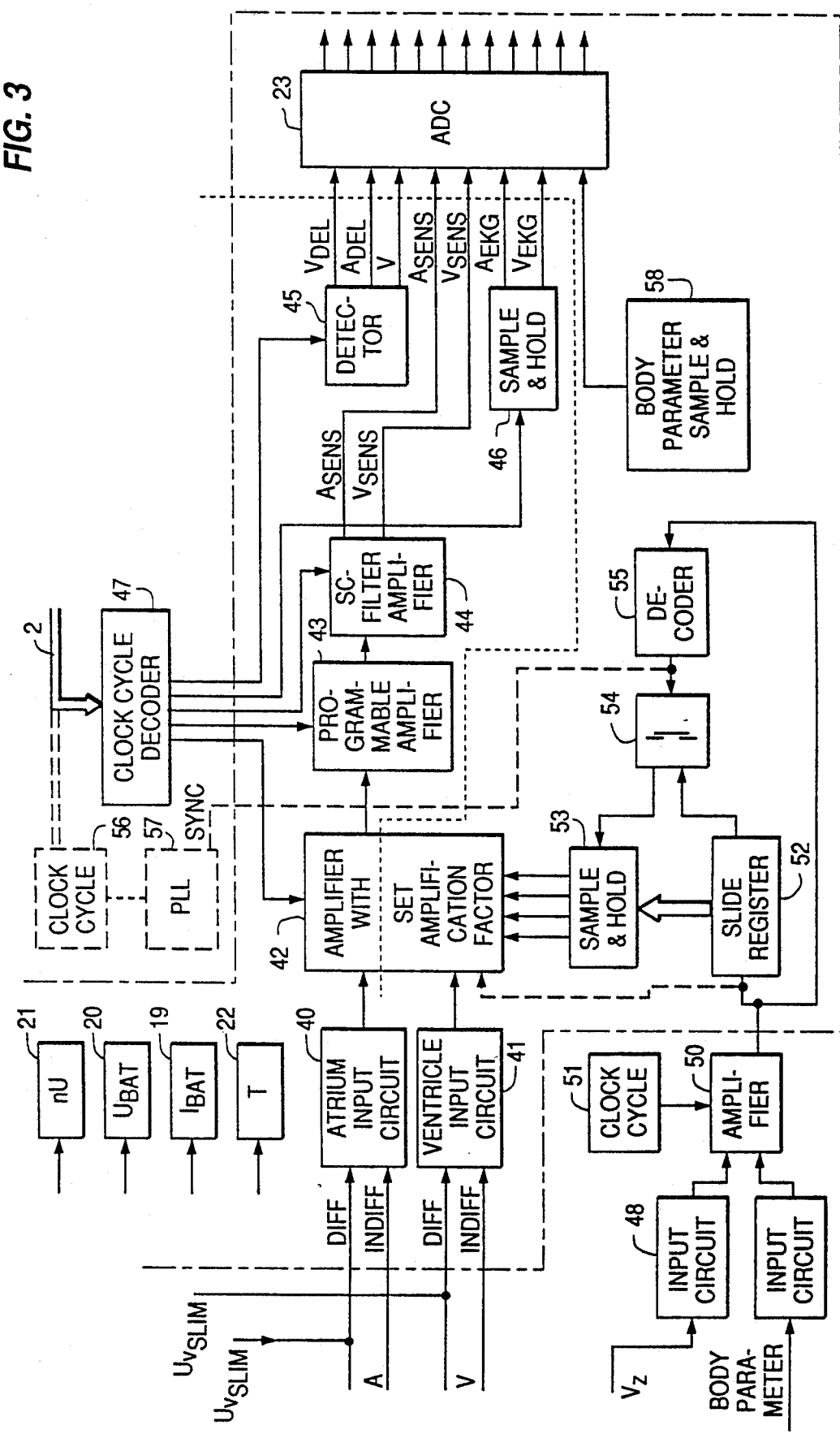

COMMON SIGNAL TRANSMISSION PATH CARDIAC PACEMAKER WITH SWITCHABLE CAPACITORS

BACKGROUND OF THE INVENTION

The invention relates to an inplantable cardiac pacemaker having a plurality of inputs for signal reception and switching means connected to the inputs.

With modern cardiac pacemakers a sequence of input signals are processed which occur at separate leads. These signals must be increased in amplitude in accordance with the signal level and if necessary must be filtered or interimly stored. For this, with the conventional cardiac pacemakers, separate input amplifiers are necessary which require a substantial construction volume and this construction volume acts contrary to the required diminshing of the outer dimensions of the implantable cardiac pacemakers. Also, in the integrated embodiment, the area covered on a silicon chip by a plurality of preamplifiers and filters is considerable. In addition, the circuits in the analog embodiment are quite complicated in comparison to digital circuits and a plurality of integrated construction elements are needed which make the additional means needed for each process channel considerable.

SUMMARY OF THE INVENTION

The object of this invention is to provide a circuit for a cardiac pacemaker which, even though the number of input channels is increased, is only slightly more complicated than the means required for just one single input channel.

The invention is based on the realization that the signals to be interpreted in the heart during signal processing with regard to the change with time require a much smaller transmission band-width than that which is supplied by the usual amplifier circuits.

Due to the time overlapping function all or nearly all of the signals relevant with regard to the operational characteristics of the cardiac pacemaker can be processed in one and the same transmission path.

A special advantage is that simultaneously with the sequential switching over between signal sources, transmission path and output connections, the transmission characteristics of the transmission path can also be switched over by switching amplification factors and/or in particular, by switching filter characteristics which is carried out by switching over the similarly synchronical switchable capacities. The switching over processes fit into the sequential clock cycle times in such a way that a switching over process of a signal path comprises differing signal paths being switched on periodically during the recurring clock cycle sequence. In addition, signals can also be transmitted for various modes of operation within a recurring clock cycle sequence so that the signals for these modes of operation with regard to the signal processing can be processed as it were "simultaneously", whereby the one signal which offers the best result is only selected in a subsequent step.

The transmission path can be used simultaneously for signal formation or for controlling during which the characteristics of the transmission path can also be altered in a controlled manner and in which a feedback occurs due to the characteristics of the lead being alterable dependent on the data transmitted via the lead, whereby in an advantageous feature the transmission path itself or else a time-sequential part of the transmission path can act as the regulation path.

In this way an optimal amplifier configuration can be achieved for implantable cardiac pacemakers. The configuration requires a minimum of external passive components and a minimal number of IC-circuits, to be able to guarantee a multiplex two chamber operation including atrial and ventricular endocardial ECG supervision and signal reception. In addition, the bipolar and unipolar operation mode is programmable and the input shut-off of the input and the sensitivity (amplification) is programmable. A multipole multiplex-bandpass-ECG-filter circuit is provided on the chip to record the R-wave and the P-wave signals.

Further advantageous features of the invention are featured in the dependent claims and will be described in greater detail below together with a description of the preferred embodiment of the invention as shown in the drawings.

BRIEF DESCRIPTION OF THE DRAWINGS

FIG. 3 is a detailed block circuit diagram of the processing part shown in FIG. 2b which includes the multiplex-transmission paths.

DETAILED DESCRIPTION OF A PREFERRED EMBODIMENT

Figure 1:
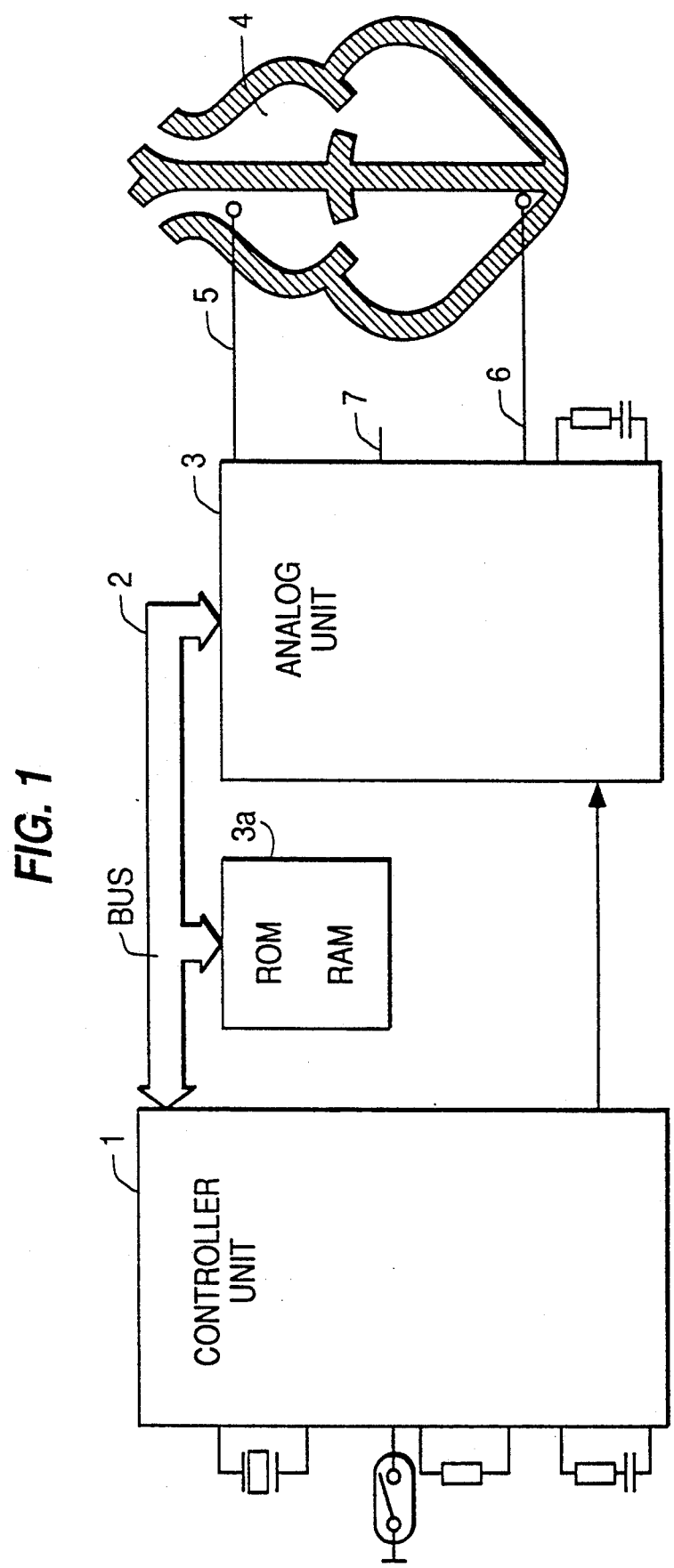
FIG. 1 a functional block diagram of an embodiment of the cardiac pacemaker according to the invention.

In the block diagram illustrated in FIG. 1 a controller unit 1 is connected to an analog unit 3 via a data bus 2. Additionally connected to the data bus 2 is a memory 3a, comprising ROM and RAM memory areas. The connection leads to the heart 4 and further sensing devices to transmit a patients body parameters are connected up with the analog unit 3. A Vorhof-electrode 5, a heart chamber electrode 6 and a further input for a sensing device 7 are shown in the illustrated embodiment. The controller unit 1 and the analog unit 3 are in connection with further element groups which will be described in further detail in the following block diagrams. The element groups shown in FIG. 1 are hermetically sealed in an implantable housing together with an energy supply unit and are provided with connectors for the external electrodes or sensing devices.

Figure 2A:
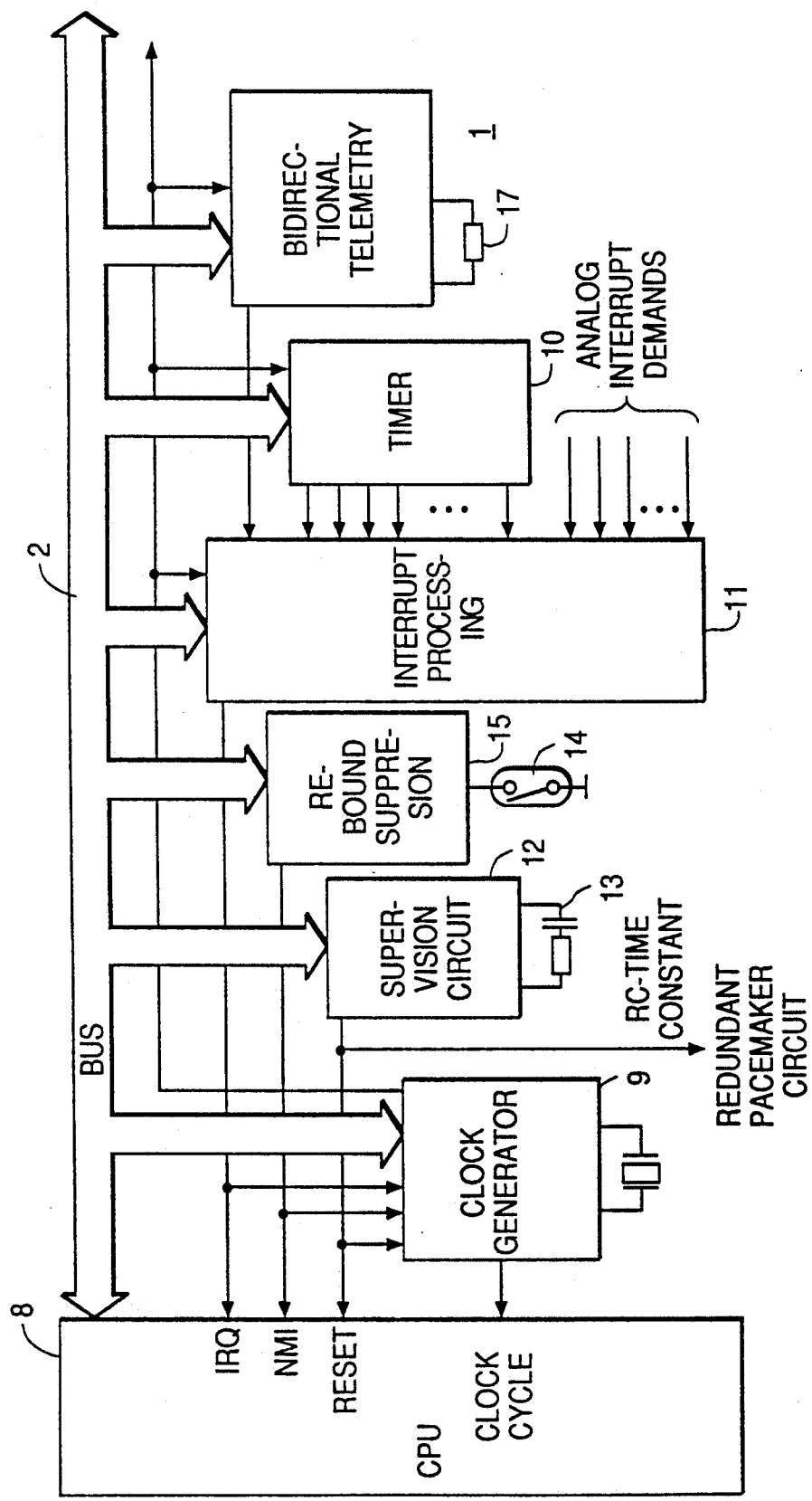
FIGS. 2a and 2b comprise a detailed block circuit diagram of that shown generally in FIG. 1.

Controller unit 1 is illustrated in FIG. 2a as including a CPU 8 provided with a system clock by way of a quartz-stabilized clock generator 9. Digital data processing steps are controlled from the CPU whereby digital data is exchanged between the various illustrated blocks via data bus 2. The CPU is in a rest position if an operation is not required to be carried out by the CPU due to external occurences or interruptions caused by a timer 10. All of the interruptions are centrally recorded by an interruption-processing unit 11 and are transmitted to the CPU vis an IRQ (Interrupt Request) lead. The known pacemaker functions can be carried out in this manner whereby the stimulation impulses can be actuated either after a predetermined time interval after a spontaneous occurence has been registered in the heart or, if these occurences do not take place, at predetermined regular time intervals. The combination of these occurences is carried out according to a set programme which is stored in memory 3 shown in FIG. 1. This programme is the basis for the control of the system and for the transmission of data between the individual blocks of the controller. It also comprises a supervision circuit 12, which further supervises the stimulation occurences by way of an RC-time constant circuit 13 and synchronizes a redundant pacemaker circuit in analog unit 3 which takes over if the digital system fails. The RC-time constant of the supervision circuit 12 enables a time comparison to be carried out which is independent of the system clock.

A conventional reed switch 14 is provided with a rebound suppression circuit 15 which makes the known magnetic switch function of cardiac pacemakers possible. In addition, connected to data bus 2 is a bi-directional telemetry circuit 16 which is in communication with an external programming unit via a coil 17 and enables not only the "programming" of the pacemaker circuitry by altering the system programmes, and in that way altering the operational parameters of the pacemaker, but also enables ECGs and pacemaker data to be transmitted out of the patient's body.

Figure 2B:
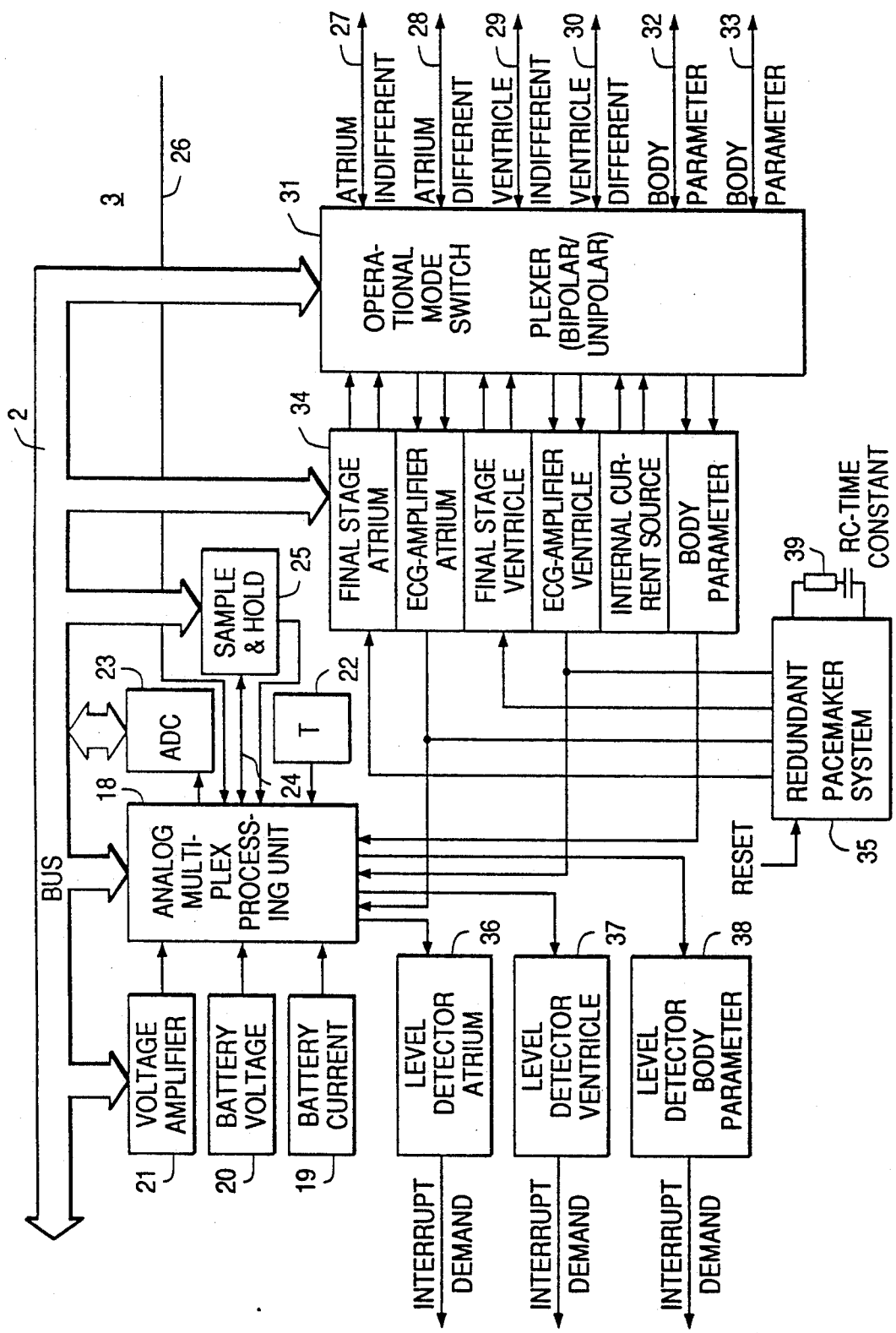

Analog unit 3 of the pacemaker according to the invention is illustrated in FIG. 2b whereby a plurality of analog parts work together with data bus 2. The central element group in this case is an analog multiplex processing unit 18 which is controlled by data bus 2 and transmits and creates a plurality of analog signals in a common channel. Clock frequency control is carried out from data bus 2 whilst the analog input and output signals travel to the analog parts described below.

Apart from the signals necessary for the pacemaker functions, additional element groups are provided to supervise the internal pacemaker functions. The functioning of the battery current 19, the battery voltage 20 and the voltage amplifier which is programmable via the data bus can be under controlled supervision by periodic detection and read-out of the output data. A further value available inside the pacemaker is the momentary body temperature of the patient which is detected by a temperature sensing device 22 and transmitted to processing unit 18. In this case it is a value which influences the rate of the pacemaker as it is a measure of the stress on the body. The same can be applied to the data relating to the power source in which case it is known that with a drop in the battery voltage some of the performance characteristics of the pacemaker can be omitted or else the impulse actuation can be carried out in a more economical fashion. The output signals of the analog multiplex processing unit 18 travel in this case to an analog-digital converter (ADC) 23. It is also shown, by way of a loop 24 that the analog signals can pass through the multiplexer processing path a plurality of times in which case a "Sample-and-hold" circuit 25 provides an interim store as this sequential processing must be carried out in a number of "processing windows" in order to prevent a feedback and for example to ensure that a varying filtering or interim storing of the signal using time constants can be carried out.

In this way a time-delayed alteration of the heartbeat-rate as a result of a change in body temperature, whilst taking the relevant time constants into account, can be copied in an analog way on the process path. Because of a low clock frequency for this processing channel, the equalizing processes in the thus formed signal filter circuits are very slow. The analog multiplex processing unit 18 is in connection with an external connector of the pacemaker via yet another lead 26 which (see below for description) already integrates the incoming data which is multiplex overlapped with regard to time into the operational time sequence of the processing unit 18.

The other output leads which are in connection with the body, such as two atrium connectors 27 and 28 and two ventricle connectors 29 and 30 can be used alternatively in the bipolar or the unipolar operational mode by switching an operational mode switch 31 which can be placed over data bus 2. Additional signals registered in the patient's body are transferred from connectors 32 and 33 via operational mode switch 31 to the relevant processing units of the pacemaker which in this case are signal inputs which are connected to the electrode input leads. The corresponding signal receivers are provided inside the electrodes which are inserted in the heart whereby operational mode switch in the 31 allows for a programme-controlled adaptation to the various sensing devices via data bus 2.

The input and output stages for heart stimulation and for signal reception via the electrode input lead are provided in a further element group 34, which can be activated via data bus 2. They are in order as follows: the final stage (output stage) for the stimulation of the atrium, the ECG amplifier (sense input)-stage for the atrium, the final stage for the ventricle, an internal current source for the impedance measurement in the heart if plethysmography is carried out and the reception circuit for the body parameters.

Whilst the impulse output final stages are either actuated via the data available from data bus 2 or else the impulses are directly actuated by an additional redundant pacemaker system 35 which is synchronized by the circuit 12 in FIG. 2a, the input stages transfer their signals onto the analog multiplex processing unit 18. These signals are then clocked and are processed consecutively with the required operational steps which will be described in greater detail using FIG. 3.

The input signals from the ECG amplifier are directly transferred to the redundant system 35 in the atrium and in the ventricle so that it can stimulate independently if the digital processing unit fails in which case an RC-time constant circuit 39 acts as the time defining element. The redundant cardiac pacemaker system is synchronized by the supervision circuit 12 in FIG. 2a via a RESET-input during the operation of the digital system in order that it can continue with the synchronized stimulation at any time.

The signals processed by the multiplex processing unit 18 are transferred to level detectors 36, 37 and 38 corresponding to each of the input signals from the atrium, ventricle or other body regions whereby the level detectors are one stage analog-digital convertors. The output signals of these detectors 36 to 38 create interruption demands at the interruption processing unit 11 in FIG. 2a.

An optimized amplifier configuration with multiplex processing for a cardiac pacemaker is illustrated in detail in the circuit diagram in FIG. 3. The part with a dashed and dotted border is the same as the illustration according to FIG. 2b with the exception of the redundant pacemaker part 35 which is not shown here.

The block diagram as shown in FIG. 3 comprises an external part with passive circuitry and an internal IC-switching circuit.

Figure 4:
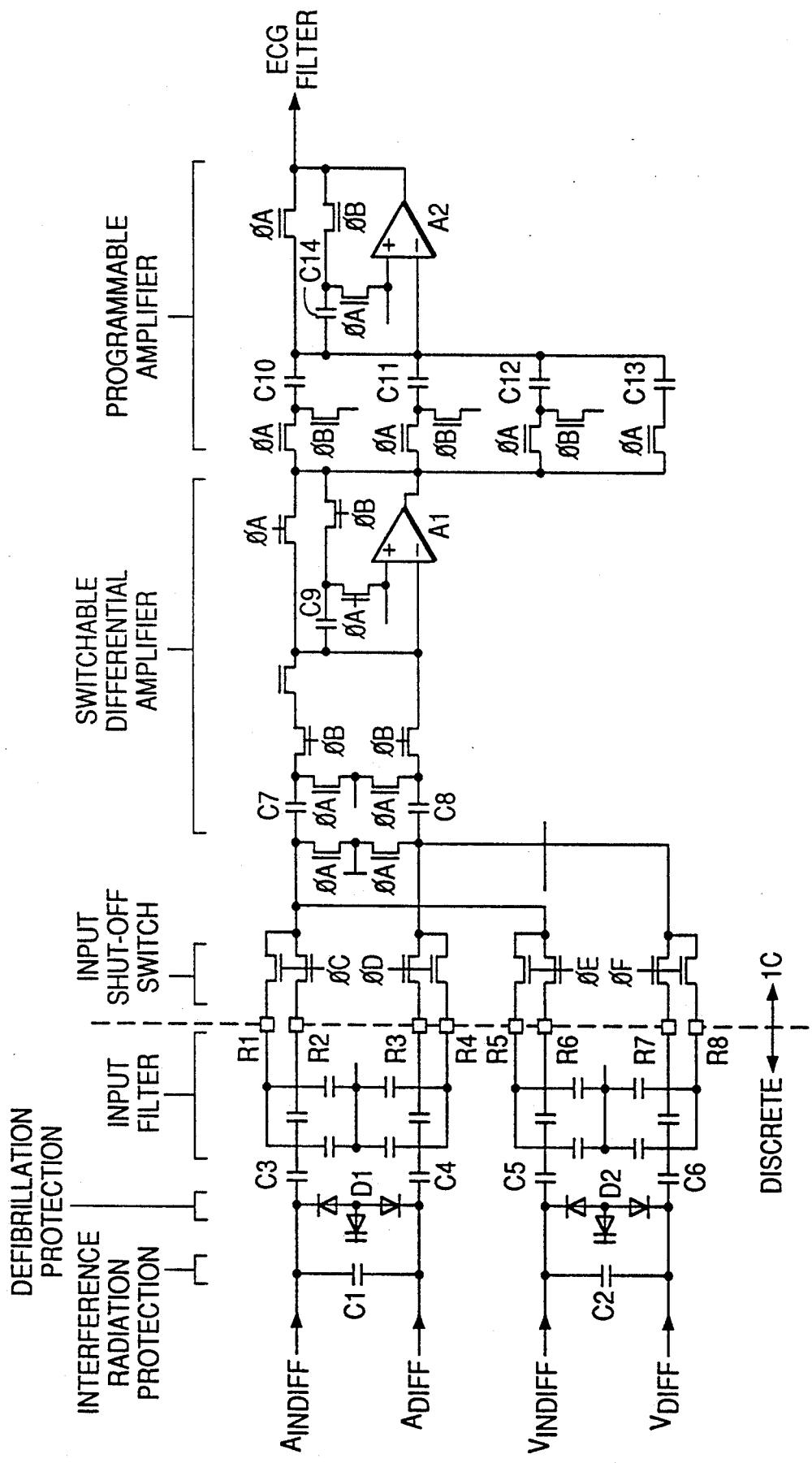
FIGS. 4 to 6 are circuit schematics which show details of the circuits of the mutiplex processing part shown in FIG. 3.
Figure 5:
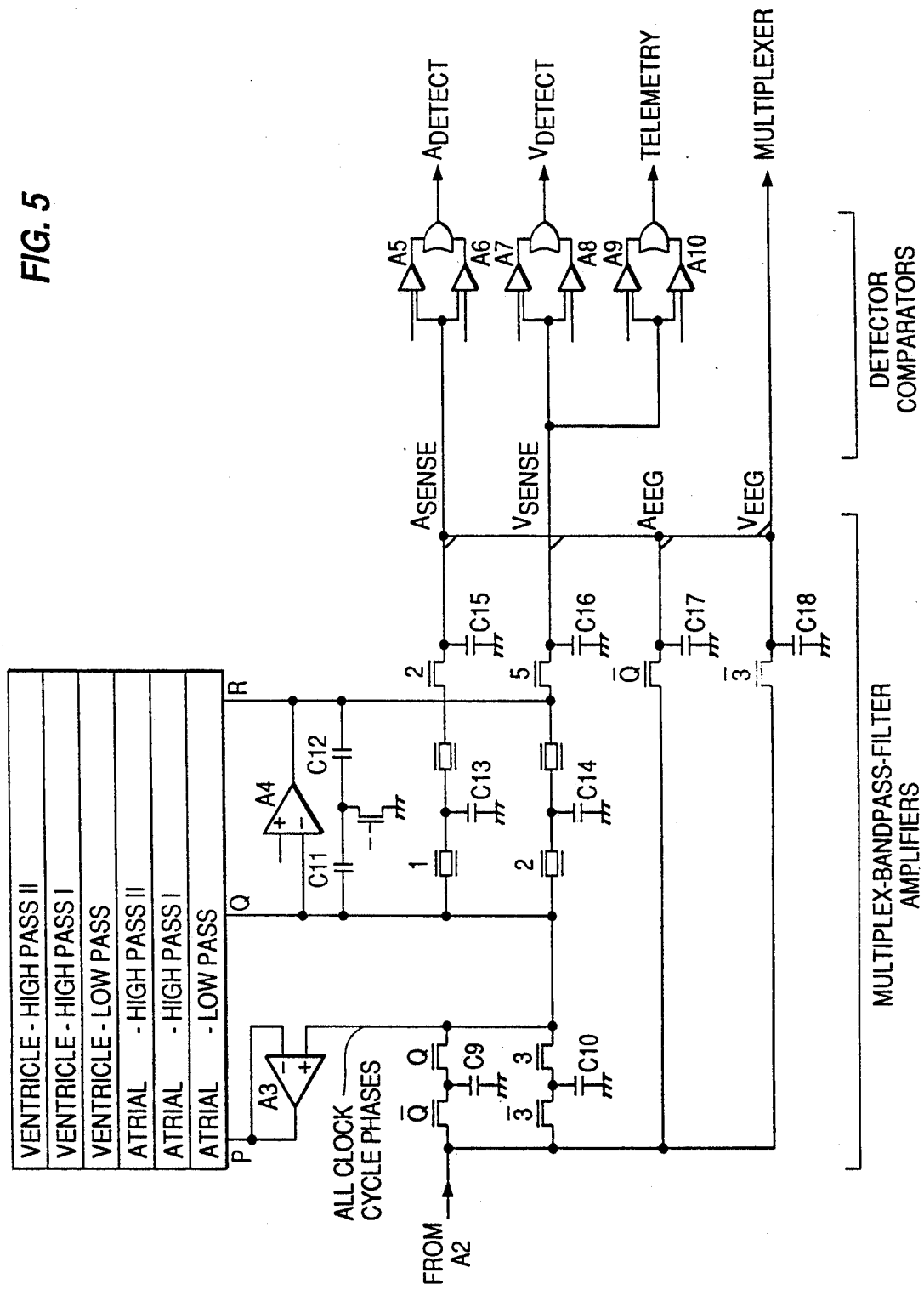
Figure 6:
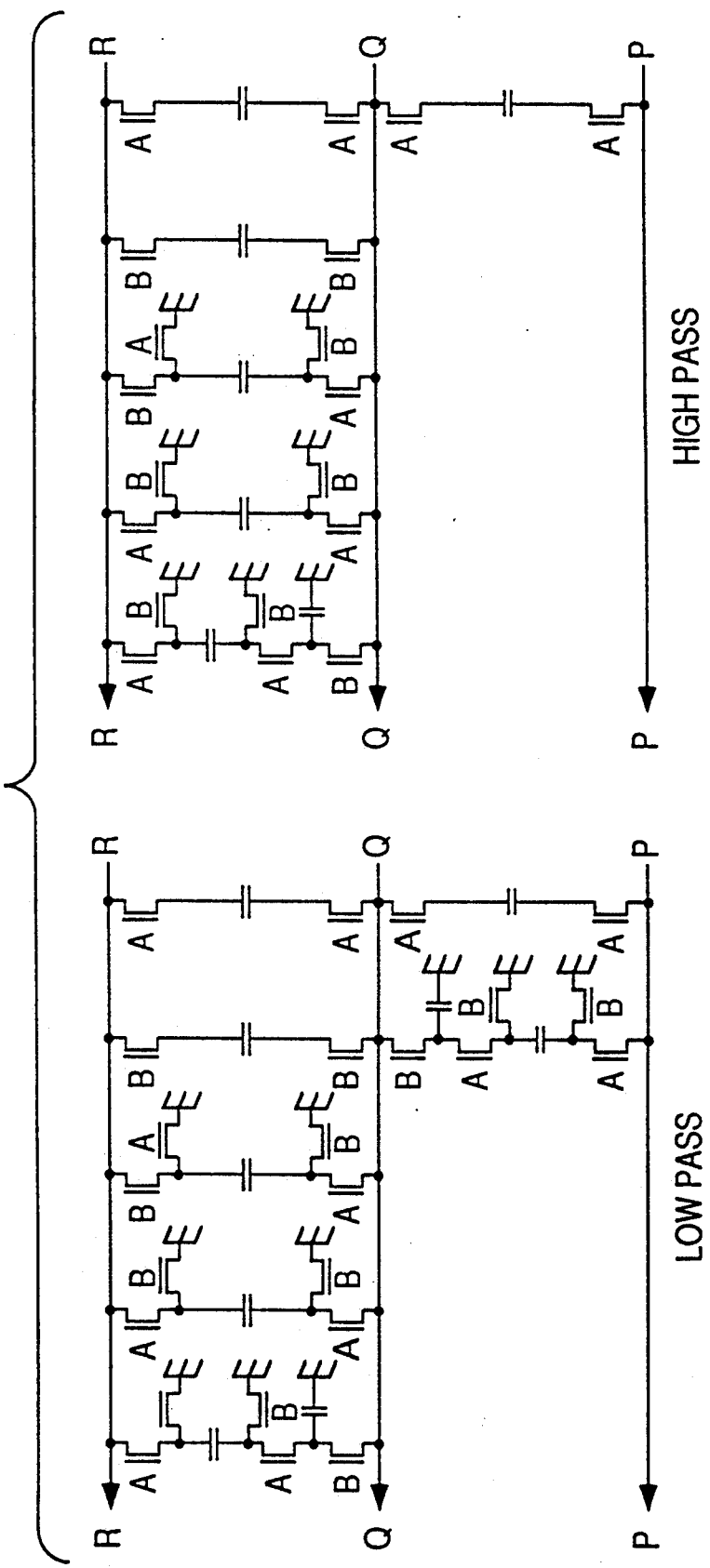

Details of the circuit configuration are illustrated by way of the chosen element groups illustrated as examples in FIGS. 4 to 6 whilst the values of the filter components are shown in table 1. The corresponding time charts are in FIG. 7.

The element groups shown in FIGS. 4 to 6 in greater detail are atrial and the ventricular input circuits 40 and 41, amplifier 42 with a set amplification factor connected to them, the then following amplifier 43 with an adjustable amplification factor, filter amplifier 44, detection circuit 45 and sample&hold circuit 46. The inputs of the next circuits named above are connected to the then following circuits named above with the exception of the circuits 40 and 41, whose output signals are both transmitted to circuit 42, and circuit 46, whose input is also connected with the output of circuit 43.

Figure 7:
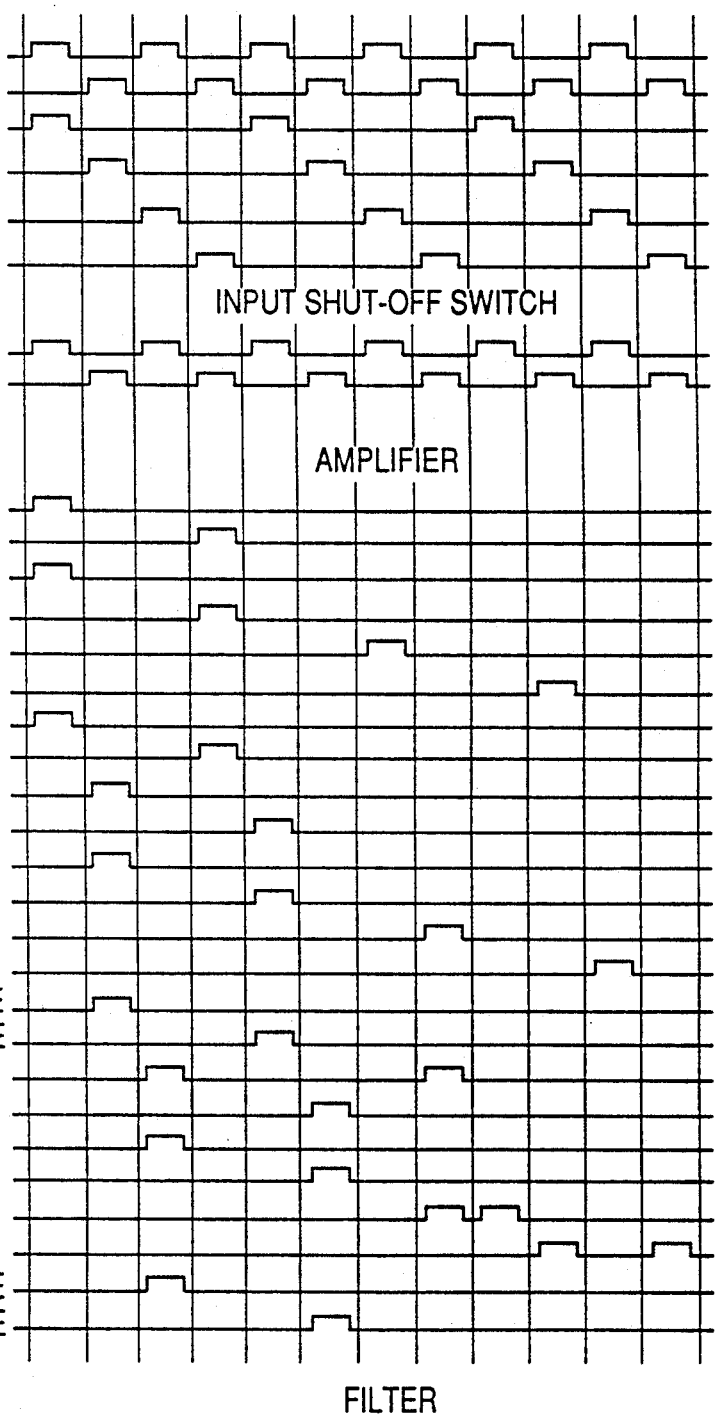
FIG. 7 is a timing chart which shows various signals helpful in explaining the invention.

A clock cycle decoder 47 creates the control signals for the individual element groups in multiplex operation using the signals obtained from data bus 2. The corresponding data bytes are created in the required sequence by the digital processing unit i.e. controller 1. A corresponding control signal from the data bus switches one of the control leads assigned to each of the element groups on or off. A clock phase chart for the element groups illustrated in FIGS. 4 to 6 is shown in FIG. 7. The timer is set using the controller programme for the next point in time when a corresponding control signal is to be transmitted to one of the element groups and when that point in time has been reached an interruption is actuated which activates the processor (CPU) which can in the meantime be inactive.

It is also possible with the circuit as illustrated in FIG. 3 to already use the multiplex signal on a lead which is connected with an external transducer or else with for example the pacemaker electrode.

Input circuits 48 and 49 which correspond in structure with the circuits 40 and 41, are provided separately and are connected on the output side with an amplifier 50 with a set amplification factor which corresponds in structure with amplifier 42. The inputs of amplifier 50 are controlled by input circuit 48 and 49 and are connected together by a clock generator 51 so that the signals, whose levels have been augmented, and as they are transmitted by circuits 48 and 49, appear in a partially cyclic fashion at the output of amplifier 50. Circuits 48 and 49 are combined together in one group element which is connected with the other pacemaker circuit, which is situated apart from them, preferably outside the housing, and is only connected with one data lead and with the leads for the power supply.

In this manner a plurality of external measurement points can be provided without having to provide leads inside the body which are very susceptible to damage and each comprising a plurality of wires. In the shown embodiment the input signal is obtained for the input circuit 48 from an additional electrode Vz which is inserted in the ventricle which enables all the signals to be received independent of a polarisation of the stimulation electrode. The signal obtained from the additional electrode Vz can also be used to supervise the backloading of an output capacitor of the stimulation circuit in the ventricle with so-called "autoshort impulses" which are directed against the stimulation impulse so as to be able to ascertain when the polarisation of the stimulation electrode has decreased to such an extent that the electrode can again be utilized to receive signal, in particular for effectivity detection.

The input of circuit 49 can be used to determine plethysmographic data which enables predictions to be made relating to the ventricular activity by analysing the electrical resistance distribution in the heart chamber.

The data which is consecutively transmitted from the element group 50 via a lead to a slide register 52 inside the pacemaker housing are transmitted to a sample&hold circuit 53 after a full data sequence has been transmitted. This transmission process is actuated by a switch 54 whose output signal actuates sample&hold circuit 53 to receive new data. Switch 54 is in turn controlled from a decoder 55 which is actuated by a signal which recurs in cyclic fashion as part of the input signal of the slide register 52 and which signals the end of a data sequence.

This signal is of a level in this illustrated embodiment which is far greater than levels of the other occuring signals and is always in contact with the input of circuit 50 in the form of a signal "++".

Due to the cyclic detection and read-out of these inputs the signal creates a reference signal as part of the consecutive cyclic signal samples. The decoder circuit 55 acts as a threshold detector which is only actuated by this reference signal ocurring in signal sequence. The output signals of sample&hold circuit 53 are detected and read-out in a cyclic manner by amplification circuit 42 via additional inputs so that the external and already multiplex transmitted signal values can be taken over by the multiplex processing of the element groups 42 to 46. In this embodiment the data which is transmitted in a multiplex operation to the pacemaker are again transmitted as separate signals existing in an analog form at a plurality of leads via circuits 52 and 53 in order that they can again be converted into multiplex signals with the circuit 42 by scanning.

In a variation (dashed illustration) the data which is multiplexed by group element 50 is included directly in the multiplex-time sequence of the group elements 42 to 45. For this, the data which is obtained at the transducers situated outside and which are multiplexed on one single lead are transmitted from the output of element group 50 on a lead which is illustrated in a dashed fashion directly to the input of the amplifier 42. This data is ordered with relation to time so that it can appear after the recognition signal which also comprises one impulse which is of a greater amplitude than the other analog parts of the signal in a time period without signal transmission which is long enough to enable all of the signals which appear at the input of the amplifier 42 to be received consecutively.

Due to the programming of the system and due to the clock decoder 47, signals are only received via the lead of the output of the element group 50 for a number of clock cycles corresponding to the number of the consecutively appearing signals on this lead. After the recognition signal the remaining inputs of the amplifier 42 are recalled in sequence within the time window in which there are no signals from the output of the circuit 50 so that all of the input signals of the circuit 50 and all of the other input signals of the circuit 42 appear in consecutive order at the output of the circuit 42 and can then be processed further in the usual manner.

The then following circuits 43 and 44 are each switched over, as is also done when processing each of the analog input signals, even though the input of the circuit 42 is still, for a number of clock cycle sequences, connected with the output of the circuit 50 situated at a distance.

A precondition for this type of operational mode is the synchronization of the clock generator 51 with the clock generator in the main system. This can be achieved by not, or not solely, controlling clock decoder 47 via data bus 2, but via a separate clock genarator 56 which in turn is controlled by a PLL system 57 and is synchronized by the output of decoder 55. The reference impulse as part of the output signals of circuit 50 guarantees that clock generator 51 is in phased synchronization with the consecutive (multiplexed) signal sequence transmitted from outside.

As the phase position of the total sequences concur due to the PLL system 57 the individual parts of the signals in the multiplex signal can also be received consecutively and in synch so that the incoming sequential signal parts from the output of circuit 50 can be exactly integrated in the time chart generated by the circuit 42.

The feedback of signals for further processing from the output of the multiplexer configuration back to its input is exemplified by the illustration of the signal which is fed back to the element group (sample&hold circuit) 58. It is the signal relating to the body temperature which is transmitted by the circuit 22. This signal is available at the output of the circuit 58. The transmission of this signal inside the multiplex signal sequence preferably only takes place at larger time intervals as the alteration rate is small. In this manner more time is available in the channel for signals which alter more rapidly or for other signals. It is often the case that not the absolute temperature value but the alteration of temperature with time or else the integral of this value is required for the signal processing in a pacemaker. For the corresponding analog processing the output signal of the element group 58 is returned back to the input of the element group 42 and is again processed in a time window by switching on the corresponding time constant (filter) elements in the circuit 44. This processing can also be carried out using a low scanning rate. In this manner the special requirements of very different analog input signals can be met in an optimal way whereby the total analog signal processing can be carried out in one single transmission channel.

Referring to FIGS. 4 and 5 the illustrated external discrete circuit will be described in detail. The element comprises input capacitors C1 and C2 which protect against electromagnetic interference. A threefold configuration of each of the performance Zener diodes D1 and D2 act as protection in the case of defibrillations. The resistors R1 to R8 and the capacitors C1 to C10 act as anti-aliasing and band limitation filters. The limiting frequencies of the input band for the differential-input-filter and for the input signal lie at about 0.5 Hz and 100 Hz.

The internal IC-circuit comprises an operational amplifier A1 with a multiplex input and a set amplification, a multiplex amplifier A2 with a programmable amplification and a multipoled band multiplex-bandpass-filter amplifier A3, A4 with a set amplification which are followed by comparators A5 to A10 which detect those signal levels which exceed set limiting values.

The amplifier A1 with a multiplex input is built using switch capacitor technology (SC),· whereby the set amplification is determined by the relationship between the input and the backfeed capacity. In the preferred embodiment the input capacity is 25 pF and the backfeed capacity is 1 pF which corresponds to a set amplification of 25.

The programme switch makes a unipolar/bipolar operation mode possible. In this way the input amplifier can either be operated like an unsymmetrical amplifier (switch open) or like a differential amplifier (switch closed). The control circuit for the phase Φ-F offers input shut-off signals for the input and protection from stimulation impulses in the same channel or from stimulation impulses in the distant fields of the other channel which occur at the sensing electrode. The operational mode of the multiplex amplifier with switched capacitors is dependent on the phase position of the capacitors which act as switches and which are controlled by a clock generator with non-overlapping impulses in time. The multiplexing of the two input signals is carried out by switching every input stage with the half of the scanning rate of the backfeed network of the amplifier with the unsymmetrical input. The switching sequence is illustrated in FIG. 7. Whilst the capacitors which act as input shut-off switches short circuit the input signal in impulses in order to eliminate interference which is created by the output signals at certain times, the switchable capacitors in the input part of the amplifier A1 at the same time create connections between the signal input leads of the amplifier and the input terminals in accordance with the known bipolar or unipolar operation.

The amplifier A2 with a programmable amplification is built using unsymmetrical, switched capacitor topology with an amplification which is defined by the relationship between the input and the feedback capacity. In the preferred embodiment the input capacity is programmable in stages of 1, 2, 4 and 8 pF. In the case that the feedback capacity is set at 0.6 pF, the amplification is programmable from 1,667 to 25 in stages of 1,667. A maximal over-all-amplification of 625 (25 times 25) is obtainable with the input amplifier and the programmable amplifier of the preferred embodiment acting together. The operation mode of the amplifier with switched capacitors is independent of the correct phase position of the switch which is controlled by the cycle generator with the non-overlapping cycles. The switching sequence is shown in FIG. 7. The switched capacities act similar to the backfeed and input resistances of a known operation amplification circuits in continuous operation.

Referring to FIG. 5 the multiplex multipole band pass filter with a set amplification will now be described in detail. It is constructed using switched capacitor technology with amplification and band pass characteristics which are set by the relationship between the capacitor elements i the backfeed network and the input network. In the preferred embodiment the output signal of the amplifier with the programmable amplification is determined by the sample&hold principle whereby the wide banded atrial and ventricular ECG signals are subdivided into two groups. The one scanned group is transmitted to the filter circuit whist the other reaches the telemetry-supervision-unit. The filter elements which determine the transmission characteristics are similar in construction with the known filter circuits for continuous operation whereby due to the switched capacities the flow of energy occurs in impulses. The switched capacities act as resistors. The capacitors which determine the frequency are built in the usual way so that these capacitors are only charged or uncharged when they are connected to the other switching points via the switched capacities. These usual capacitors therefore store their charges until they are again "served" consecutively. Between these sequential clock cycle times their condition is unchangeable i.e. "frozen" if one disregards natural decharging.

The scanned broad band ECG input signals are held and filtered consecutively by the filter circuit and the multipoled backfeed network in order to obtain filtered atrial and ventricular ECG output signals. These output signals are not only transmitted to the telemetry supervision switching circuits but also to the detector switching circuits. The multiplex filter is created in an unsymmetrical amplifier topology whereby two atrial high pass regions and an atrial low pass region are provided as well as two ventricular high pass regions and one ventricular low pass region. The consecutive phase switching of the switches is controlled by a clock generator with non-overlapping impulses. The consecutive phase positions of the clock signals of the high pass and low pass filters create the required filtered multiplex output signals. The switching impulse sequence is shown in FIG. 7. The consecutive operational mode of the switches and of the high pass or low pass filter regions create filtered output signals with +80 dB/per decade in the deep frequency region and −40 dB/per decade in the high frequency region.

Each fiter circuit contributes 40 dB/decade so that each channel requires two high pass networks and one low pass network to create the desired filter characteristics.

The corner frequencies are set by the relationship between the capacitors in each filter circuit whereby the −3 dB corner frequencies are set at 40 and 100 for the Vorhof and are set at 20 and 60 Hz for the ventricle.

The feedback paths of the filter circuits as shown in FIG. 5 (upper blocks) are illustrated in FIG. 6.

Regarding the connection paths between the element groups illustrated in the FIGS. 4 to 6, refer to the circuit diagrams. With regard to the switching on times of the switched capacities, refer to the correspondingly marked time intervals and the associated descriptions of the operation functions in question. It can be seen that some of the switchable capacitors are clocked—i.e activated—with every second clock cycle impulse in the impulse sequence, whilst other capacitor groups are activated every four, eight or twelve impulses. In this way, due to the consecutive operational mode, reproduced branched signal paths can be again branched during reproduction or can separate into three further paths (corresponding to a clocking with every eighth or twelfth signal impulse). If, for example, the signals received from the ventricle or the atrium are processed in the same amplification and filter path, then differing amplification and filter characteristics can be set for each of the atrium and ventricle signals. The diversity of this "subdivision" of the signal processing paths is defined by the upper limiting frequency required during signal transmission, as at most the frequencies to be transmitted are impaired by the consecutive transmission.

The illustrated circuits comprise overlapping connection paths of the switching configurations which can be activated consecutively, whereby the capacitors switched in clock cycles act as the switching elements in the connection paths which are activated periodically and consecutively. In frequency defining circuits, such as filters, the capacitors act at the same time as the frequency defining switching elements, since their values are chosen so that they form differing dynamic resistances with reference to the clock cycle times.

The alteration of the transmission characteristics of the multiplex transmission path can be carried out via the digital part via the corresponding switching condition of the switched capacitor in question, dependent on the evaluation of the transmitted data in the corresponding sequential "channel".

In this manner an amplitude regulation and also an alteration of the filter characteristics is possible dependent on the signal amplitudes in the lead. The lead with its complex switchable transmission characteristics can, on one or more time-defined transmission channels due to a programmed transmission characteristic for its time sequence, act as a "controller" or as any other element which comprises time-constants or filter characteristics, as can generally be described using complex transmission functions.

The present invention is not limited in its embodiments to the above-described preferred embodiment. Rather, a number of variations are conceivable which take advantage of the described solution even for basically different configurations.

I claim:

1. In an implantable cardiac pacemaker including a pacemaker housing and a plurality of inputs receiving analog signals from external and internal signal sources, the improvement comprising:
   a common signal transmission path; and
   switching means, comprising an integrated circuit including integrated switchable capacitors, within the housing coupled to the received analog signals for switching the received analog signals for consecutive, multiplex transmission on the common signal transmission path at least inside the housing.

2. A pacemaker as defined in claim 1, further comprising circuit means coupled to said switching means along the common signal transmission path for altering transmission characteristics of the analog signals in synchronism with the switching of the received analog signals to the common signal transmission path.

3. A pacemaker as defined in claim 2, wherein said circuit means includes switchable capacitors.

4. A pacemaker as defined in claim 3, wherein said circuit means comprises filter circuits including said switchable capacitors which have capacitances that determine characteristics of said filter circuits.

5. A pacemaker as defined in claim 3, wherein said circuit means includes amplification switching circuits in the common signal transmission path having amplification factors that can be altered by switching over input capacity or feedback capacity by way of said switchable capacitors.

6. A pacemaker as defined in claim 1, and further comprising a digitally operational system means connected to said switching means for generating switching signals that are used by said switching means to switch over the received analog signals to the common signal transmission path.

7. A pacemaker as defined in claim 6, wherein said digitally operational system means includes a data bus and a decoder connected to the data bus for decoding data on the data bus for generating the switching signals.

8. A pacemaker as defined in claim 6, further including individual signal sources on the common signal transmission path, wherein said digitally operational system means includes means for altering a frequency with which said individual signal sources are switched on.

9. A pacemaker as defined in claim 6, further comprising analog to digital converters having inputs coupled to the common signal transmission path for receiving in sequence signals from the common signal transmission path.

10. A pacemaker as defined in claim 9, wherein said digitally operational system means includes a digital processor and said analog to digital converters comprise threshold level detectors means which, on reaching a set signal amplitude value, produce interruption signals that are transmitted to said digital processor.

11. A pacemaker as defined in claim 1, and further comprising a sample and hold circuit having an input connected in sequence with the common signal transmission path.

12. A pacemaker as defined in claim 1, wherein the signal sources include atrial and ventricular electrodes.

13. A pacemaker as defined in claim 1, wherein the signal sources include means for producing signals representing characteristic body signals, independent of cardiac electrical signal potential, including at least one of body temperature, blood pressure, sound, plethysmographic, photometric, mechanical and chemical signals.

14. A pacemaker as defined in claim 1, wherein the pacemaker includes a stimulation electrode and a further electrode for electrically contacting the heart wall in the ventricle.

15. A pacemaker as defined in claim 1, and further comprising one of a battery and voltage amplifier current circuit including either a current or voltage transducer.

16. A pacemaker as defined in claim 1, and further comprising an interim memory means having an input and an output each being connected to said common signal transmission path at differing points in time for time altering signals transmitted on said common signal transmission path.

17. A pacemaker as defined in claim 16, wherein at least at one of the differing points in time the transmission path comprises a complex transmission function.

18. A pacemaker as defined in claim 1, wherein said common signal transmission path includes a lead to the pacemaker outside said housing.

19. A pacemaker as defined in claim 18, further comprising multiplexing means for multiplexing signals on the lead outside said housing and for combining the multiplexed signals from said lead in a consecutive manner with signals already on the common signal transmission path inside said housing.

20. A pacemaker as defined in claim 1, and further comprising means for switching over from bipolar to unipolar electrode connection by way of switchable capacitors.

21. A pacemaker as defined in claim 1, and further including digital means for digitally controlling amplification and filter characteristics of signals on said common signal transmission path so that when a threshold value is exceeded by a signal the signal is attenuated and when the threshold value exceeds the signal, the signal is amplified.

* * * * *